(12) United States Patent
Manoharan

(10) Patent No.: US 6,277,967 B1
(45) Date of Patent: Aug. 21, 2001

(54) CARBOHYDRATE OR 2'-MODIFIED OLIGONUCLEOTIDES HAVING ALTERNATING INTERNUCLEOSIDE LINKAGES

(75) Inventor: Muthiah Manoharan, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/115,025

(22) Filed: Jul. 14, 1998

(51) Int. Cl.$^7$ ............................ C12Q 1/68; C07H 19/00; C07H 21/00; C07H 21/02; C07H 21/04
(52) U.S. Cl. ............ 536/22.1; 536/23.1; 536/24.3; 536/24.31; 536/24.33; 536/25.3; 536/25.32; 435/6; 435/91.1; 435/91.2
(58) Field of Search .................. 536/22.1, 23.1, 536/24.3, 24.31, 25.3, 25.31, 25.32; 435/6, 91.1, 91.2

(56) References Cited

U.S. PATENT DOCUMENTS

| | | | |
|---|---|---|---|
| 3,687,808 | 8/1972 | Merigan et al. | 195/28 |
| 4,689,320 | 8/1987 | Kaji | 514/44 |
| 4,806,463 | 2/1989 | Goodchild et al. | 435/5 |
| 5,004,810 | 4/1991 | Draper | 536/27 |
| 5,166,195 | 11/1992 | Ecker | 514/44 |
| 5,194,428 | 3/1993 | Agrawal et al. | 514/44 |
| 5,212,295 | 5/1993 | Cook | 536/26.7 |
| 5,220,007 * | 6/1993 | Pederson et al. | 536/23.1 |
| 5,242,906 | 9/1993 | Pagano et al. | 514/44 |
| 5,248,670 | 9/1993 | Draper et al. | 514/44 |
| 5,264,423 | 11/1993 | Cohen et al. | 514/44 |
| 5,442,049 | 8/1995 | Anderson et al. | 536/24.5 |
| 5,457,189 | 10/1995 | Crooke et al. | 536/24.5 |
| 5,514,577 | 5/1996 | Draper et al. | 435/238 |
| 5,514,788 | 5/1996 | Bennett et al. | 536/23.1 |
| 5,523,389 | 6/1996 | Ecker et al. | 536/23.1 |
| 5,580,767 | 12/1996 | Cowsert et al. | 435/172.3 |
| 5,582,972 | 12/1996 | Lima et al. | 435/6 |
| 5,582,986 | 12/1996 | Monia et al. | 435/6 |
| 5,587,361 | 12/1996 | Cook et al. | 514/44 |
| 5,591,600 | 1/1997 | Ecker | 435/69.1 |
| 5,591,623 | 1/1997 | Bennett et al. | 435/240.2 |
| 5,591,720 | 1/1997 | Anderson et al. | 514/44 |
| 5,599,797 | 2/1997 | Cook et al. | 514/44 |
| 5,607,923 | 3/1997 | Cook et al. | 514/44 |
| 5,620,963 | 4/1997 | Cook et al. | 514/44 |
| 5,658,891 | 8/1997 | Draper et al. | 514/44 |
| 5,661,134 | 8/1997 | Cook et al. | 514/44 |
| 5,681,747 | 10/1997 | Boggs et al. | 435/375 |
| 5,681,944 | 10/1997 | Crooke et al. | 536/24.5 |
| 5,691,461 | 11/1997 | Ecker et al. | 536/24.32 |

FOREIGN PATENT DOCUMENTS

| | | |
|---|---|---|
| WO 93/07883 | 4/1993 | (WO) . |
| WO 93/18052 | 9/1993 | (WO) . |
| WO 94/08003 | 4/1994 | (WO) . |
| WO 95/13834 A1 | 5/1995 | (WO) . |

OTHER PUBLICATIONS

Akhtar et al. "Stability of antisense DNA oligodeoxynucleotide analogs in cellular extracts and sera" Life Sciences, vol. 49, pp. 1793–1801, 1991.*

Albert, P.R. et al., "Antisense knockouts: molecular scalpels for the dissection of signal transduction", *Trends Pharmacol. Sci.*, 1994, 15, 250–254.

(List continued on next page.)

*Primary Examiner*—Jezia Riley
(74) *Attorney, Agent, or Firm*—Woodcock Washburn Kurtz Mackiewicz & Norris LLP

(57) ABSTRACT

Noel compounds that mimic and/or modulate the activity of wild-type nucleic acids. In general, the compounds are oligonucleotides which contain at least one region of 2'-modified nucleosides connected by alternating phosphodiester and phosphorothioate linkages.

27 Claims, 1 Drawing Sheet

OTHER PUBLICATIONS

Baker, B.F. et al., "2'-O-(2-Methoxy)ethyl-modified Anti-intercellular Adhesion Molecule 1 (ICAM-1) Oligonucleotides Selectively Increase the ICAM-1 Translation Initiation Complex in Human Umbilical Vein Endothelial Cells", *J. Biol. Chem.*, 1997, 272, 11994–12000.

Berkow et al. (eds.) *The Merck Manual of Diagnosis and Therapy*, 15th Edition, Rahway, N.J., 1987, 2301–2310.

Berkow et al. (eds.) *The Merck Manual of Diagnosis and Therapy*, 15th Edition, Rahway, N.J., 1987, 2263–2277.

Berkow et al. (eds.), *The Merck Manual of Diagnosis and Therapy*, 15th Edition, Rahway, N.J., 1987, 2283–2287.

Berkow et al. (eds.), *The Merck Manual of Diagnosis and Therapy*, 15th Edition, Rahway, N.J., 1987, 2286–2292.

Bernhard et al., "Direct Evidence Linking Expression of Matrix Metalloproteinase 9 (92–kDa gelatinase/collagenase) to the metastatic phenotype in transformed rat embryo cells," *Proc. Natl. Acad. Sci. U.S.A.*, 1994, 91, 4293–4297.

Birkedal–Hansen, "Proteolytic Remodeling of Extracellular Matrix," *Curr. Op. Cell Biol.*, 1995, 7, 728–735.

Boggemeyer et al., "Borrelia Burgdorferi Upregulates the Adhesion Molecules E–selectin, P–selectin, ICAM–1 and VCAM–1 on Mouse Endothelioma Cells in vitro," *Cell Adhes. Commun.*, 1994, 2, 145–157.

Cook, P.D., "Medicinal chemistry of antisense oligonucleotides—future opportunities", *Anti–Cancer Drug Design*, 1991, 6, 585–607.

Crooke. S.T. et al., "Pharmacokinetic Properties of Several Novel Oligonucleotide Analogs in mice", *J. Pharmacol. Exp. Therapeutics*, 1996, 277, 923–937.

Crooke, S.T. et al., "Progress in Antisense Oligonucleotide Therapeutic", *Ann. Rev. Pharmacol. Toxicol.*, 1996, 36, 107–129.

Dean, N.M. et al., "Inhibition of protein kinase C–α expression in mice after systemic administration of phosphorthioate antisense oligodeoxynucleotides", *Proc. Natl. Acad. Sci.*, 1994, 91, 11762–11766.

DeLisser et al., "Molecular and Functional Aspects of PECAM–1/CD31," *Immunol. Today*, 1994, 15, 490–494.

Downward,"The ras Superfamily of Small GTP–binding proteins," *TIBS*, 15, 1990, 469–472.

Englisch, U. et al., "Chemically Modified Oligonucleotides as Probes and Inhibitors", *Angew. Chem. Int. Ed. Eng.*, 1991, 30, 613–629.

Griffiths, C.E.M. et al., "Keratinocyte Intercellular Adhesion Molecule–1 (ICAM–1) Expression Preceedes Derman T Lymphocyte Infiltration in Allergic Contact Dermatitis (*Rhus dermatitis*)", *Am. J. Pathology.*, 1989, 135, 1045–1053.

Gum et al., "Stimulation of 92–kDa Gelatinase B Promoter Activity by ras Is Mitogen–activated Protein Kinase Kinase 1–independent and Requires Multiple Transcription Factor Binding Sites Including Closely Spaced PEA3/ets and AP–1 Sequences," *J. Biol. Chem.*, 1996, 271, 10672–10680.

Hakugawa et al., "The Inhibitory Effect of Anti–Adhesion Molecule Antibodies on Eosinophil Infilration in Cutaneous Late Phase Response inn Balb/c Mice Sensitized with Ovalbumin (OVA)," *J. Dermatol.*, 1997, 24, 73–79.

Hegemann, L. et al., "Biochemical Pharmacology of Protein Kinase C and its Relevance for Dermatology", *Pharmacology of the Skin*, Mukhtar. H. (ed.), CRC Press, Boca Raton, 1992, Ch.22, 357–268.

Himelstein et al., "Proteases and Their Inhibitors in Invasion and Metastasis, Metalloproteinases in Tumor Progression: The Contribution of MMP–9," *Invasion Metastasis*, 1994–95, 14, 246–258.

Ho, V.C. et al., "Treatment of severe lichen planus with cyclosporine", *J. Am. Acad. Dermatol.*, 1990, 22, 64–68.

Hua et al., "Inhibition of Matrix Metalloproteinase 9 Expression by a Ribozyme Blocks Metastasis in a Rat Scarcoma Model System," *Cancer Res.*, 1996, 56, 5279–5284.

Hurtenbach et al., "Prednisolone Reduces Experimental Arthritis and Inflammatory Tissue Destruction in Scid Mice Infected with *Borrelia burgdorferi*," *Int. J. Immunopharmac*, 1996, 18, 281–288.

Kabanov, A.V.,"A new class of antivirals: antisense oligonucleotides combined with a hydrophobic substituent effectively inhibit influenza virus reproduction and synthesis of virus–specific proteins in MDCK cells", *FEBS Letts.*, 1990, 259, 327–330.

Katocs, A.S. et al., "Biological Testing", *Remington's Pharmaceutical Sciences*, 18th Ed., Gennaro (ed.) Mack Publishing Co., Easton, PA, 1990, Ch. 27, 484–494.

Kerr et al., "TGF–B1 Inhibition of Transin/Stromelysin Gene Expression Is Mediated Through a Fos Binding Sequence," *Cell*, 1990, 61, 267–278.

Kerr et al., "Growth Factors Regulate Transin Gene Expression by c–fos–Dependent and c–fos–Independent Pathways." *Science*, 1988, 242, 1424–1427.

Kroschwitz, J.I., "Polynucleotides", *Concise Encyclopedia of Polymer Science and Engineering*, 1990, John Wiley & Sons, New York. 858–859.

Letsinger, R.L. et al., "Cholesteryl–conjugated oligonucleotides: Synthesis, properties and activity as inhibitors of replication of human immnodeficiency virus in cell culture", *Proc. Natl. Acad. Sci.*, 1989, 86, 6553–6556.

Lisby, S. et al., "Intracellular adhesion molecule–1 (ICAM–1) expression correlated to inflammation", *Br. J. Dermatol.*, 1989, 120, 479–484.

Litwin et al., "Novel Cytokine–independent Induction of Endothelial Adhesion Molecules Regulated by Platlet/Endothelial Cell Adhesion Molecule (CD31)," *The Journal of Cell Biology*, 1997, 139, 219–228.

Manoharan, M. et al., "Introduction of a Lipophilic Thioether Tether in the Minor Groove of Nucleic Acids for Antisense Applications", *Bioorg. Med. Chem. Letts.*,1993, 3, 2765–2770.

Manoharan, M. et al., "Chemical Modifications to Improve Uptake and Bioavailability of Antisense Oligonucleotides", *Annals NY Acad. Sciences*, 1992, 660, 306–309.

Manoharan M. et al., "Cholic Acid–Oligonucleotide Conjugates for Antisense Applications", *Bioorganic Med. Chem. Letts.*, 1994, 4, 1053–1060.

Manoharan, M. et al., "Lipidic Nucleic Acids", *Tetrahedron Letts.*, 1995, 36, 3651–3654.

Manoharan M. et al."Oligonucleotide Conjugates: Alteration of the Pharmacokinetic Properties of Antisense Agents", *Nucleosides and Nucleotides*, 1995, 14, 969–973.

Martin, P., "Ein nuer Zugang zu 2'–O–Alkylribonucleosiden und Eigenschaften deren Oligonucleotide", *Helvetic Chemica Acta*, 1995, 78, 486–504 (English summary included).

Meyer, R.B. et al., "Efficient, Specific Cross–Linking and Clevage of DNA by Stable, Synthetic Complementary Oligodeoxynucleotides", *J. Am. Chem. Soc.*, 1989, 111, 8517–8519.

Newman, "The Biology of PECAM-1," *J. Clin. Invest.*, 1997, 99, 3–7.

Nies, A.S. et al., "Principles of Therapeutics", *Goodman &Gilman's The Pharmacological Basis of Therapeutics*, 9th Ed., Hardman et al. (eds.), McGraw–Hill, New York, NY, 1996, Ch. 3, 43–62.

Oberhauser, B. et al., "Effective incorporation of 2'–O–methyl–oligonucleotides into liposomes and enhanced cell association through modification with thiocholesterol", *Nucl. Acids. Res.*, 1992, 20, 533–538.

Regezi et al., "Vasclar Adhesion Molecules in Oral Lichen Planus,"*Oral Surg. Oral Med. Oral Pathol.*, 1996, 81, 682–690.

Ruoslahti, "Fundamental Understandings: How Cancer Spreads," *Sci. Am.*, 1996, 72–77.

Saison–Behmoaras, T. et al., "Short modified antisense oligonucleotides directed against Ha–ras point mutation induce selective cleavage of the mRNA and inhibit T24 cells proliferation", *EMBO J.*, 1991, 10, 1111–1118.

Sanghvi, Y.S., "Heterocyclic Base Modifications in Nucleic acids and their Applications in Antisense Oligonucleotides", *Antisense Research and Applications*, 1993, Chapter 15, CRC Press, Boca Raton, 273–288.

Secrist, J.A. et al., "Synthesis and Biological Activity of 4'–Thionucleosides", *10th International Rountable: Nucleosides, Nucleotides and their Biological Applications*, Sep. 16–20 1992, *Abstract 21*, Park City, Utah 40.

Shea, R.G. et al., "Synthesis, hybridization properties and antiviral activity of lipid–oligodeoxynucleotide conjugates", *Nucl. Acids. Res.*, 1990, 18, 3777–3783.

Shiohara et al., "Fixed drug Eruption: Expression of Epidermal Keratinocyte Intercellular Adhesion Molecule–1 (ICAM–1)", *Arch. Dermatol.*, 1989, 125, 1371–1376.

Smith–Jones, P.M. et al., "Antibody Labeling with Copper–67 Using the Bifunctional Macrocycle 4–[(1,4,8, 11–Tetraazacyclotetrade–1–yl)methyl] benzoic Acid", *Bioconjugate Chem.*, 1991, 2, 415–421.

Stetler–Stevenson et al., "Tumor Cell Interactions with the Extracellular Matrix During Invasion and Metastasis," *Annu. Rev. Cell Biol.*, Palade, G.E. et al. (eds.), 1993, 9, 541–573.

Studer, M. et al., "One–Step Synthesis of Mono–N–substituted Azamacrocycles with a Carboxylic Group in the Side–Chain and their complexes with $Cu^{2+}$ and $Ni^{2+}$", *Helvetica Chimica Acta*, 1986, 69, 2081–2086.

Svinarchuk, F.P. et al., "Inhibition of HIV proliferation in MT–4 cells by antisense oligonucleotide conjugated to lipophilic groups", *Biochimie*, 1993, 79, 49–54.

U.S. Congress, Office of Technology Assessment, "The State–of–the–art in Genetic Screening", *Genetic Monitoring and Screening in the Workplace*, OTA–BA–455, U.S. Government Printing Office, Washington, D.C., 1990, Ch. 5, 77–99.

Wahlestedt, C. et al., "Modulation of Anxiety and Neuropeptide Y–Y1 Receptors by Antisense Oligodeoxynucleotides", *Science*, 1993, 259, 528–531.

Wahlestedt, C. et al., "Antisense oligodeoxynucleotides to NMDA–R1 receptor channel protect cortical neurons from excitotoxicity and reduce focal ischaemic infarctions", *Nature*, 1993, 363, 260–263.

Zhang, Z. et al., "Uptake of N–(4'–pyridoxyl)amines and release of amines by renal cells: A model for transporter–enhanced delivery of bioactive compounds", *Proc. Natl. Acad. Sci.*, 1991, 88, 10407–10410.

Furdon et al., "Rnase H Clevage of RNA Hybridized to Oligonucleotides Containing Methylphosphonate, Phosphorothioate and Phosphodiester Bonds", *Nucleic Acids Research*, 1989, 17, pp. 9193–9204.

Patil et al., "Synthesis&Properties of Oligothymidylate Analogus Containing Stereoregulated Phosphorothioate and Phosphodiester Linkages in an Alternating Manner", *Bioorganic&Medicinal Chem. Letters*, 1994, 4, pp. 2263–2666.

* cited by examiner

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<221> NAME/KEY: modified_base
<222> LOCATION: (1)..(20)
<223> OTHER INFORMATION: Alternating phosphodiester/phosphorothioate
      linkages
<221> NAME/KEY: modified_base
<222> LOCATION: (2)..(20)
<223> OTHER INFORMATION: 2'-Methoxyethoxy
<223> OTHER INFORMATION: Description of Artificial Sequence: Novel
      Sequence

<400> SEQUENCE: 1
tctgagtagc agaggagctc                                                     20

<210> SEQ ID NO 2
<211> LENGTH: 20
<212> TYPE: DNA
<213> ORGANISM: Artificial Sequence
<220> FEATURE:
<221> NAME/KEY: modified_base
<222> LOCATION: (1)..(20)
<223> OTHER INFORMATION: Alternating phosphodiester/phosphorothioate
      linkages
<221> NAME/KEY: modified_base
<222> LOCATION: (1)..(6)
<223> OTHER INFORMATION: 2'-Methoxyethoxy
<221> NAME/KEY: modified_base
<222> LOCATION: (15)..(20)
<223> OTHER INFORMATION: 2'-Methoxyethoxy
<223> OTHER INFORMATION: Description of Artificial Sequence: Novel
      Sequence

<400> SEQUENCE: 2
atgcattctg cccccaagga                                                     20

<210> SEQ ID NO 3
<211> LENGTH: 20
<212> TYPE: DNA
<213> ORGANISM: Artificial Sequence
<220> FEATURE:
<221> NAME/KEY: modified_base
<222> LOCATION: (1)..(20)
<223> OTHER INFORMATION: Alternating phosphodiester/phosphorothioate
      linkages
<221> NAME/KEY: modified_base
<222> LOCATION: (13)..(20)
<223> OTHER INFORMATION: 2'-Methoxyethoxy
<223> OTHER INFORMATION: Description of Artificial Sequence: Novel
      Sequence

<400> SEQUENCE: 3
gcccaagctg gcatccgtca                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 4
tctgagtagc agaggagctc                                                     20

```
<210> SEQ ID NO 5
<211> LENGTH: 20
<212> TYPE: DNA
<213> ORGANISM: Artificial Sequence
<220> FEATURE:
<221> NAME/KEY: modified_base
<222> LOCATION: (1)..(20)
<223> OTHER INFORMATION: All phosphorothioate linkages
<223> OTHER INFORMATION: Description of Artificial Sequence: Novel
      Sequence

<400> SEQUENCE: 5
tctgagtagc agaggagctc                                                    20

<210> SEQ ID NO 6
<211> LENGTH: 20
<212> TYPE: DNA
<213> ORGANISM: Artificial Sequence
<220> FEATURE:
<221> NAME/KEY: modified_base
<222> LOCATION: (1)..(20)
<223> OTHER INFORMATION: All phosphorothioate linkages
<221> NAME/KEY: modified_base
<222> LOCATION: (1)..(20)
<223> OTHER INFORMATION: 2'-Methoxyethoxy
<223> OTHER INFORMATION: Description of Artificial Sequence: Novel
      Sequence

<400> SEQUENCE: 6
tctgagtagc agaggagctc                                                    20

<210> SEQ ID NO 7
<211> LENGTH: 20
<212> TYPE: DNA
<213> ORGANISM: Artificial Sequence
<220> FEATURE:
<221> NAME/KEY: modified_base
<222> LOCATION: (1)..(20)
<223> OTHER INFORMATION: 2'-Methoxyethoxy
<223> OTHER INFORMATION: Description of Artificial Sequence: Novel
      Sequence

<400> SEQUENCE: 7
tctgagtagc agaggagctc                                                    20

<210> SEQ ID NO 8
<211> LENGTH: 20
<212> TYPE: DNA
<213> ORGANISM: Artificial Sequence
<220> FEATURE:
<221> NAME/KEY: modified_base
<222> LOCATION: (1)..(20)
<223> OTHER INFORMATION: Alternating phosphodiester/phosphorothioate
      linkages
<221> NAME/KEY: modified_base
<222> LOCATION: (1)..(20)
<223> OTHER INFORMATION: Staggered 2'-Methoxyethoxy
<223> OTHER INFORMATION: Description of Artificial Sequence: Novel
      Sequence

<400> SEQUENCE: 8
tctgagtagc agaggagctc                                                    20

<210> SEQ ID NO 9
<211> LENGTH: 20
<212> TYPE: DNA
<213> ORGANISM: Artificial Sequence
<220> FEATURE:
<221> NAME/KEY: modified_base
```

```
<222> LOCATION: (1)..(20)
<223> OTHER INFORMATION: 2'-Methoxyethoxy
<221> NAME/KEY: modified_base
<222> LOCATION: (2)
<223> OTHER INFORMATION: c=5-methyl
<221> NAME/KEY: modified_base
<222> LOCATION: (10)
<223> OTHER INFORMATION: c=5-methyl
<221> NAME/KEY: modified_base
<222> LOCATION: (18)
<223> OTHER INFORMATION: c=5-methyl
<221> NAME/KEY: modified_base
<222> LOCATION: (20)
<223> OTHER INFORMATION: c=5-methyl
<223> OTHER INFORMATION: Description of Artificial Sequence: Novel
      Sequence

<400> SEQUENCE: 9
tctgagtagc agaggagctc                                                    20

<210> SEQ ID NO 10
<211> LENGTH: 20
<212> TYPE: DNA
<213> ORGANISM: Artificial Sequence
<220> FEATURE:
<221> NAME/KEY: modified_base
<222> LOCATION: (4)
<223> OTHER INFORMATION: c=5-methyl
<221> NAME/KEY: modified_base
<222> LOCATION: (6)
<223> OTHER INFORMATION: c=5-methyl
<221> NAME/KEY: modified_base
<222> LOCATION: (9)
<223> OTHER INFORMATION: c=5-methyl
<221> NAME/KEY: modified_base
<222> LOCATION: (13)
<223> OTHER INFORMATION: c=5-methyl
<223> OTHER INFORMATION: Description of Artificial Sequence: Novel
      Sequence

<400> SEQUENCE: 10
gatcgcgtcg gactatgaag                                                    20

<210> SEQ ID NO 11
<211> LENGTH: 20
<212> TYPE: DNA
<213> ORGANISM: Artificial Sequence
<220> FEATURE:
<221> NAME/KEY: modified_base
<222> LOCATION: (1)..(20)
<223> OTHER INFORMATION: 2'-Methoxyethoxy
<221> NAME/KEY: modified_base
<222> LOCATION: (1)..(20)
<223> OTHER INFORMATION: All phosphorothioate linkages
<221> NAME/KEY: modified_base
<222> LOCATION: (2)
<223> OTHER INFORMATION: c=5-methyl
<221> NAME/KEY: modified_base
<222> LOCATION: (10)
<223> OTHER INFORMATION: c=5-methyl
<221> NAME/KEY: modified_base
<222> LOCATION: (18)
<223> OTHER INFORMATION: c=5-methyl
<221> NAME/KEY: modified_base
<222> LOCATION: (20)
<223> OTHER INFORMATION: c=5-methyl
```

```
<223> OTHER INFORMATION: Description of Artificial Sequence: Novel
      Sequence

<400> SEQUENCE: 11
tctgagtagc agaggagctc                                                    20

<210> SEQ ID NO 12
<211> LENGTH: 20
<212> TYPE: DNA
<213> ORGANISM: Artificial Sequence
<220> FEATURE:
<221> NAME/KEY: modified_base
<222> LOCATION: (4)
<223> OTHER INFORMATION: c=5-methyl
<221> NAME/KEY: modified_base
<222> LOCATION: (6)
<223> OTHER INFORMATION: c=5-methyl
<221> NAME/KEY: modified_base
<222> LOCATION: (9)
<223> OTHER INFORMATION: c=5-methyl
<221> NAME/KEY: modified_base
<222> LOCATION: (13)
<223> OTHER INFORMATION: c=5-methyl
<223> OTHER INFORMATION: Description of Artificial Sequence: Novel
      Sequence

<400> SEQUENCE: 12
gatcgcgtcg gactatgaag                                                    20

<210> SEQ ID NO 13
<211> LENGTH: 20
<212> TYPE: DNA
<213> ORGANISM: Artificial Sequence
<220> FEATURE:
<221> NAME/KEY: modified_base
<222> LOCATION: (1)..(20)
<223> OTHER INFORMATION: 2'-methoxyethoxy
<221> NAME/KEY: modified_base
<222> LOCATION: (1)..(20)
<223> OTHER INFORMATION: Alternating phosphodiester/phosphorothioate
      linkages
<221> NAME/KEY: modified_base
<222> LOCATION: (2)
<223> OTHER INFORMATION: c=5-methyl
<221> NAME/KEY: modified_base
<222> LOCATION: (10)
<223> OTHER INFORMATION: c=5-methyl
<221> NAME/KEY: modified_base
<222> LOCATION: (18)
<223> OTHER INFORMATION: c=5-methyl
<223> OTHER INFORMATION: Description of Artificial Sequence: Novel
      Sequence

<400> SEQUENCE: 13
tctgagtagc agaggagctc                                                    20
```

CARBOHYDRATE OR 2'-MODIFIED OLIGONUCLEOTIDES HAVING ALTERNATING INTERNUCLEOSIDE LINKAGES

FIELD OF THE INVENTION

This invention relates to the design and synthesis of nuclase resistant phosphorothioate oligonucleotides which are useful for therapeutics, diagnostics and as research reagents. Oligonucleotides are provided which contain at least one region of 2'-modified nucleosides connected by alternating phosphodiester and phosphorothioate linkages. Such compounds are resistant to nuclease degradation and are capable of modulating the activity of DNA and RNA.

BACKGROUND OF THE INVENTION

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such protein is desired. By interfering with the production of proteins, the maximum therapeutic effect can be obtained with minimal side effects. It is therefore a general object of such therapeutic approaches to interfere with or other-wise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as therapeutic agents in human clinical trials against various disease states, including use as antivial agents.

In addition to such use as both indirect and direct regulators of proteins, oligonucleotides also have found use in diagnostic tests. Such diagnostic tests can be performed using biological fluids, tissues, intact cells or isolated cellular components. As with gene expression inhibition, diagnostic applications utilize the ability of oligonucleotides to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides are also widely used as research reagents. They are useful for understanding the function of many other biological molecules as well as in the preparation of other biological molecules. For example, the use of oligonucleotides as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides, both natural and synthetic, are employed as primers in such PCR technology.

Oligonucleotides are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

A number of chemical modifications have been introduced into oligonucleotides to increase their usefulness in diagnostics, as research reagents and as therapeutic entities. Such modifications include those designed to increase binding to a target strand (i.e. increase melting temperatures, Tm), to assist in identification of an oligonucleotide or an oligonucleotide-target complex, to increase cell penetration, to stabilize against nucleases and other enzymes that degrade or interfere with the structure or activity of the oligonucleotides, to provide a mode of disruption (terminating event) once sequence-specifically bound to a target, and to improve the pharmacokinetic properties of the oligonucleotide.

The complementarity of oligonucleotides has been used for inhibition of a number of cellular targets. Complementary oligonucleotides are commonly described as being antisense oligonucleotides. Various reviews describing the results of these studies have been published including Progress In Antisense Oligonucleotide Therapeutics, Crooke, S. T. and Bennett, C. F., *Annu. Rev. Pharmacol. Toxicol.*, 1996, 36, 107–129. These oligonucleotides have proven to be powerful research tools and diagnostic agents. Certain oligonucleotides that have been shown to be efficacious are currently in human clinical trials.

The pharmacological activity of oligonucleotides, like other therapeutics, depends on a number of factors that influence the effective concentration of these agents at specific intracellular targets. One important factor for oligonucleotides is the stability of the species in the presence of nucleases. It is unlikely that unmodified, naturally-occurring oligonucleotides will be useful therapeutic agents because they are rapidly degraded by nucleases. The limitations of available methods for modification of the phosphate backbone of unmodified oligonucleotides have led to a continuing and long felt need for other modifications which provide resistance to nucleases and satisfactory hybridization properties for antisense oligonucleotide diagnostics and therapeutics.

SUMMARY OF THE INVENTION

The present invention provides compounds that mimic and/or modulate the activity of wild-type nucleic acids. In general, the compounds contain a selected sequence of covalently bound nucleosides which is specifically hybridizable with a targeted nucleoside sequence of single stranded or double stranded DNA or RNA.

In some preferred embodiments, compounds are provided that comprise a plurality of covalently-bound 2'-modified nucleosides having the formula:

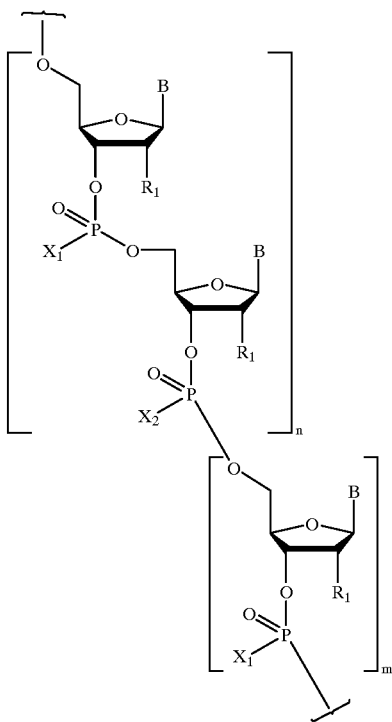

wherein:
each B is a nucleobase;
one of $X_1$ or $X_2$ is O, and the other of $X_1$ or $X_2$ is S;
each $R_1$ is F, or a group of formula $Z$—$R_{22}$—$(R_{23})_v$;
$Z$ is O, S, NH, or N—$R_{22}$—$(R_{23})_v$;
$R_{22}$ is $C_1$–$C_{20}$ alkyl, $C_2$–$C_{20}$ alkenyl, or $C_2$–$C_{20}$ alkynyl;
$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;
v is from 0 to about 10;
or $R_{21}$ has one of the formulas:

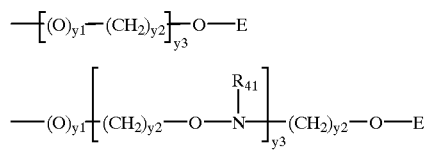

wherein:
y1 is 0 or 1;
y2 is 0 to 10;
y3 is 1 to 10;

$E$ is $N(R_{41})(R_{42})$ or $N=C (R_{41})(R_{42})$;
each $R_{41}$ and each $R_{42}$ is independently H, $C_1$–$C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heterotom selected from N and O;
n is from 2 to 50; and
m is 0 or 1.

Also provided in accordance with the present invention are oligonucleotides having the Formula:

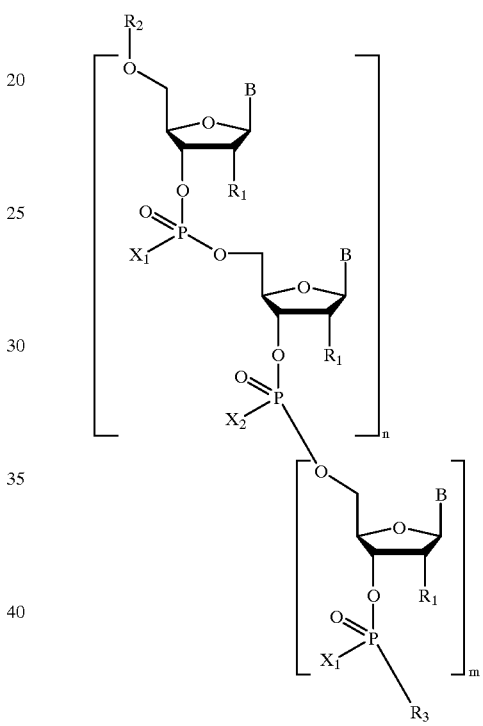

wherein:

$X_1$ is S; $X_2$ is O; $R_2$ is H, a hydroxyl protecting group, or an oligonucleotide; $R_3$ is OH, an oligonucleotide, or a linker connected to a solid support; and the other constituent variables are as defined above.

In some preferred embodiments, $R_2$ is a phosphodiester-linked oligonucleotide or a phosphorothioate linked oligonucleotide. In further preferred embodiments, $R_3$ is a phosphodiester-linked oligonucleotide or a phosphorothioate linked oligonucleotide. In still further preferred embodiments, $R_2$ and $R_3$ are each a phosphodiester-linked oligonucleotide or a phosphorothioate linked oligonucleotide.

The present invention also provides compounds having the Formula:

(5') $W^1$—$W^2$—$W^3$ (3')

wherein:

$W^1$ has the Formula:

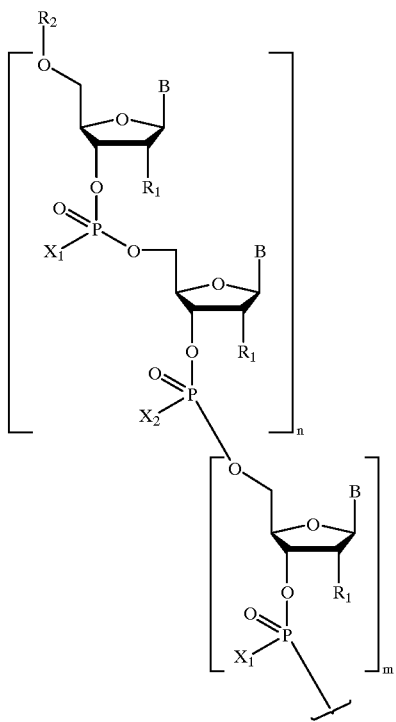

wherein one of $X_1$ or $X_2$ is O, and the other of $X_1$ or $X_2$ is S; and the other constituent variables are as defined above;

$W^3$ has the Formula:

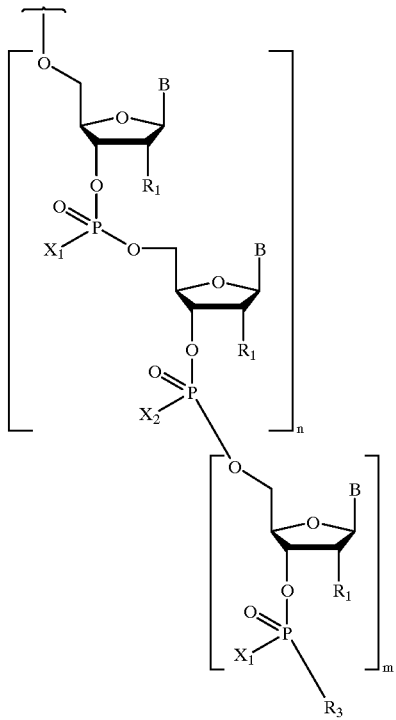

wherein $R_3$ is OH, an oligonucleotide, or a linker connected to a solid support; and $W^2$ is a plurality of covalently bound nucleosides linked by phosphodiester or phosphorothioate linkages. In some preferred embodiments, $W^2$ is a plurality of covalently bound 2'-deoxy nucleosides linked by phosphodiester or phosphorothioate linkages.

In some preferred embodiments of the compounds and methods described herein, $R_1$ is —O—$CH_2$—$CH_2$—O—$CH_3$.

In further preferred embodiments of the compounds and methods of the invention, n is about 5 to about 50, with 8 to about 30 being more preferred, 4 to about 15 being even more preferred, and 2 to about 10 being especially preferred.

In some preferred embodiments, $R_2$ is H, and $R_3$ is OH.

The present invention also provides methods for modulating the production or activity of a protein in an organism, and methods for treating an organism having a disease characterized by the undesired production of a protein. Such methods involve contacting the organism with one or more of the foregoing compounds.

Also provided are methods for assaying a nucleic acid comprising the step of contacting a solution suspected to contain the nucleic acid with at least one such compound,

DETAIL DESCRIPTION OF THE PREFERRED EMBODIMENTS

Figure 1:
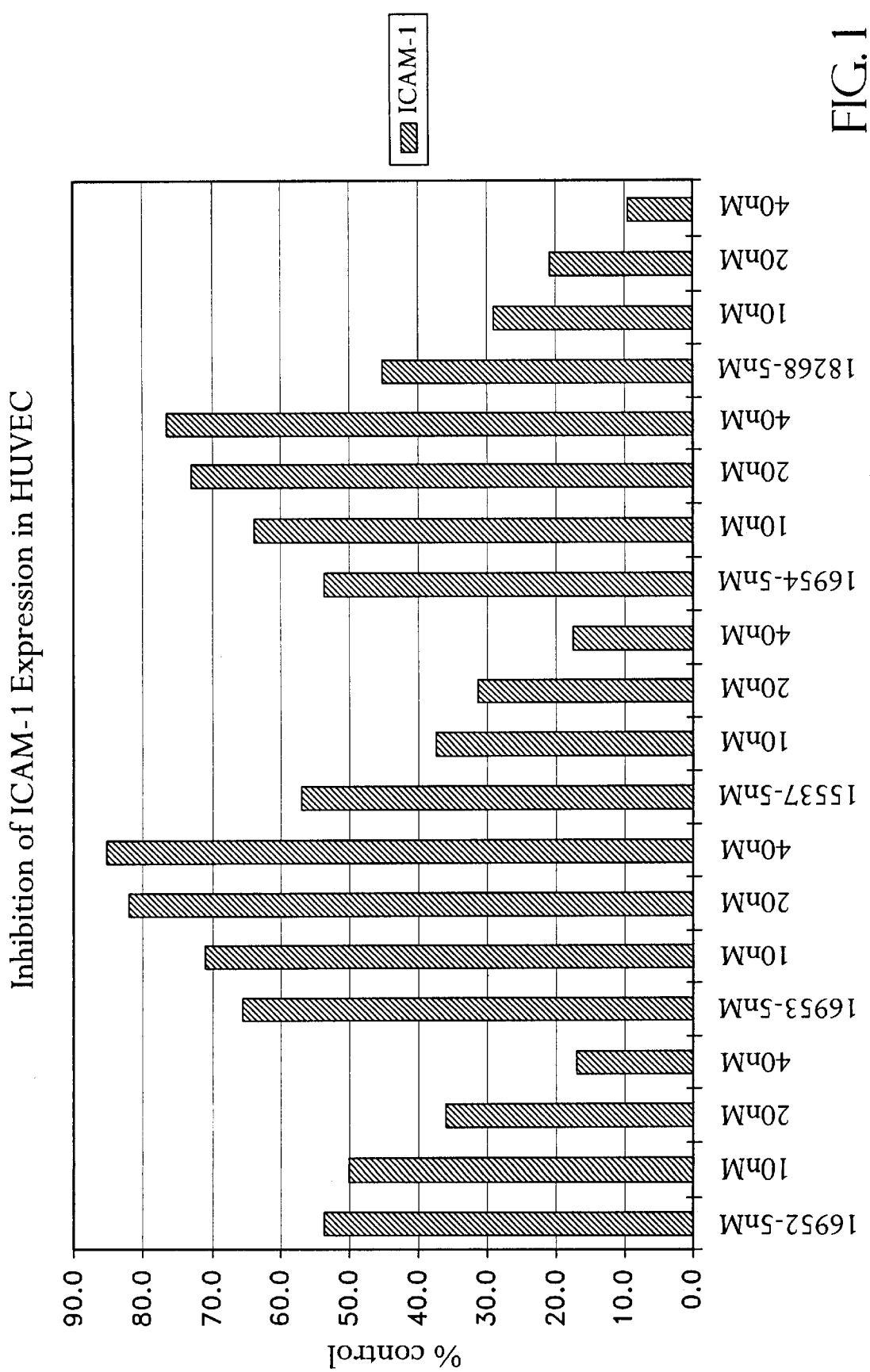
FIG. 1 shows the inhibition of ICAM-1 expression in HUVEC by compounds of the invention and control compounds.

The present invention provides oligonucleotides that contain at least one region of 2'-modified nucleosides connected by alternating phosphodiester and phosphorothioate linkages. In some preferred embodiments, the compounds have the comprise a plurality of covalently-bound 2'-modified nucleosides having the formula:

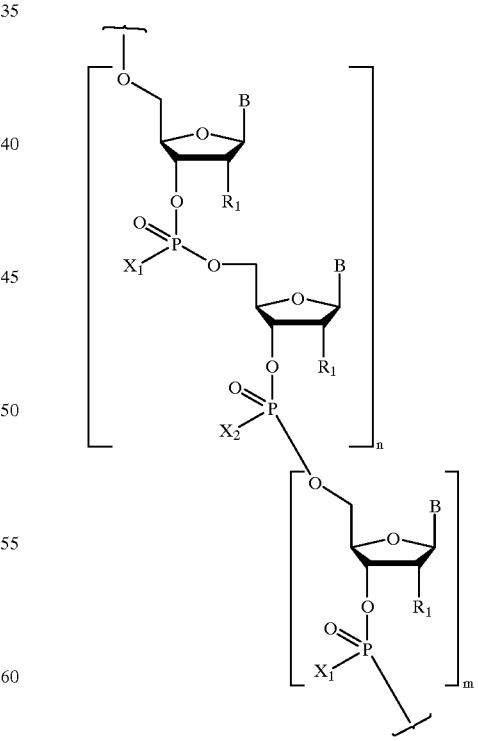

wherein:
  each B is a nucleobase;
  one of $X_1$ or $X_2$ is O, and the other of $X_1$ or $X_2$ is S;

each $R_1$ is F, or a group of formula $Z—R_{22}—(R_{23})_v$;
Z is O, S, NH, or $N—R_{22}—(R_{23})_v$;
$R_{22}$ is $C_1–C_{20}$ alkyl, $C_2–C_{20}$ alkenyl, or $C_2–C_{20}$ alkynyl;
$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialky , O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;
v is from 0 to about 10;
or $R_{21}$ has one of the formulas:

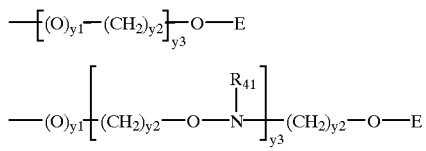

wherein:
y1 is 0 or 1;
y2 is 0 to 10;
y3 is 1 to 10;
E is $N(R_{41})(R_{42})$ or $N=C(R_{41})(R_{42})$;
each $R_{41}$ and each $R_{42}$ is independently H, $C_1–C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heterotom selected from N and O;
n is from 2 to 50; and
m is 0 or 1.

It is known that phosphorothioate linkages are essential for certain pharmacological properties of oligonucleotides, such as nuclease resistance. However, excessive numbers of phosphorothioate linkages are thought to create toxicity problems for drug compounds, for example by create some non-sequence specific side effects. It has been discovered that compounds represented by the formulas provided herein beneficially possess both improved nuclease resistance relative to uniform phosphodiester oligomers, and increase binding affinity relative to phosphorothioate oligomers. In addition, the oligonucleotides described herein may have reduced toxicity relative to uniform phosphorothioate oligonucleotides.

The addition of phosphodiester linkages to phosphorothioate oligonucleotides is expected to favorably alter the pharmacokinetics of the oligonucleotide (for example, with respect to urinary excretion, preferred distribution to kidney). The staggered phosphorothioate/phosphodiester linkages also will modulate the protein binding to plasma proteins (serum, albumin, etc.).

Further, phosphorothioate uptake has been proposed to occur by several mechanisms. One such mechanism that has been proposed is receptor mediated endocytosis. A further proposed mechanism is a shuttling mechanism, in which phosphorothioate oligonucleotides will shuttle between proteins based on their relative affinities. Thus, controlling the number of phosphorothioate linkages present in an oligonucleotide, in accordance with the present invention, can be crucial for uptake, antisense activity, and pharmacokinetics of such oligonucleotides.

While not wishing to be bound by a particular mechanism, it is believed that oligonucleotides of the present invention which have possess at least one region of uniform phosphodiester and/or phosphorothioate linkages function by a RNAase H dependent mechanism, in which hybridization leads to cleavage of the duplex by RNAse H. It is also believed that oligonucleotides of the present invention which have a uniform alternating phosphodiester/phosphorothioate backbone (i.e., oligonucleotides in which the entire backbone, or substantially the entire backbone) is composed of alternating phosphodiester/phosphorothioate linkages) do not function by a RNAase H dependent mechanism, but rather primarily 13–15 by a translation arrest mechanism.

The plurality of covalently-bound 2'-modified nucleosides, can form the entire oligonucleotide, or a part thereof. Thus, the plurality of covalently-bound 2'-modified nucleosides can be located at the 3'-terminal portion of an oligonucleotide, the 5'-terminal portion of an oligonucleotide, or at any position in between. Thus, in some preferred embodiments of the invention, oligonucleotides are provided having the Formula:

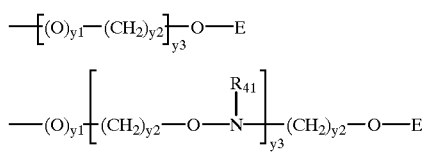

wherein:
$X_1$ is S; $X_2$ is O; $R_2$ is H, a hydroxyl protecting group, or an oligonucleotide; $R_3$ is OH, an oligonucleotide, or a linker connected to a solid support; and the other constituent variables are as defined above.

In the formula above, $R_2$, $R_3$ or both can be a phosphodiester-linked oligonucleotide or a phosphorothioate linked oligonucleotide.

The present invention also provides compounds having the Formula:

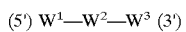

(5') $W^1—W^2—W^3$ (3')

wherein:
W¹ has the Formula:

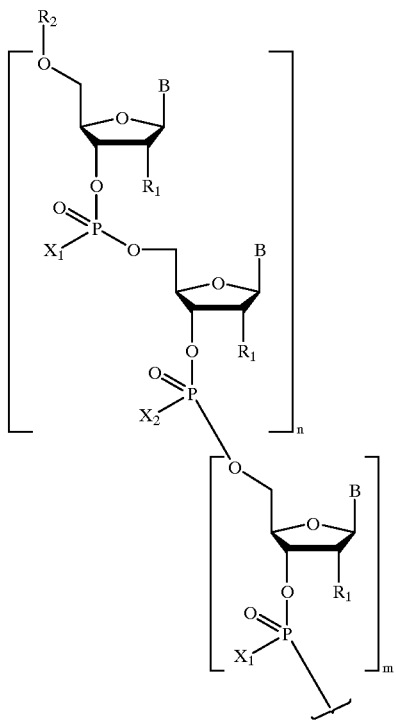

wherein one of $X_1$ or $X_2$ is O, and the other of $X_1$ or $X_2$ is S; and the other constituent variables are as defined above;
W³ has the Formula:

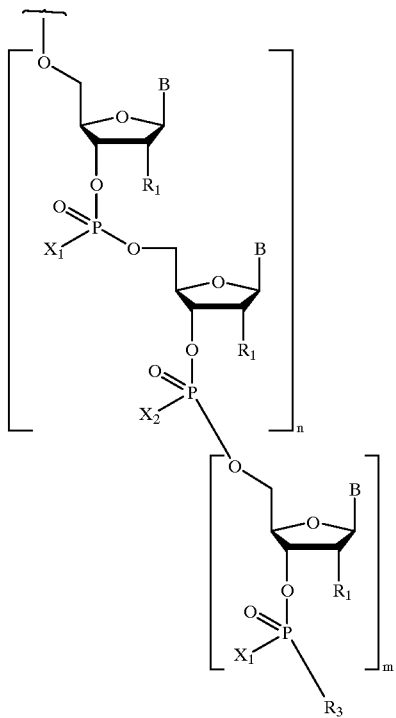

wherein $R_3$ is OH, an oligonucleotide, or a linker connected to a solid support; and W² is a plurality of covalently bound nucleosides linked by phosphodiester or phosphorothioate linkages. In some preferred embodiments, W² is a plurality of covalently bound 2'-deoxy nucleosides linked by phosphodiester or phosphorothioate linkages.

In some especially preferred embodiments of the compounds and methods described herein, the 2'-substituent represented by $R_1$ is a —O-ethyl-O-methyl ("MOE") group.

In some especially preferred embodiments, the region of alternating phosphodiester/phosphorothioate linkages occurs at least one terminal of the oligonucleotide. It is especially preferred that the terminal nucleotide of such region have a phosphorothioate linkage.

The compounds of the invention can have appended thereto any of a variety of molecular conjugate species that serve to facilitate uptake, targeting or efficacy of the oligonucleotide. Representative conjugate moieties include phospholipids, cholesterol, folic acid, vitamins, steroids, and their derivatives. Additional conjugate species include proteins, peptides, alkylators, lipophilkic molecules, intercalators, cell receptor binding molecules, crosslinking agents and other groups for modifying properties of oligomers which include RNA cleaving complexes, pyrenes, metal chelators, porphyrins, hybrid intercalator/ligands and photo-crosslinking agents. RNA cleavers include o-phenanthroline/Cu complexes and $Ru(bipyridine)_3^{2+}$ complexes. The $Ru(bipyridine)_3^{2+}$ complexes interact with nucleic acids and cleave nucleic acids photochemically. Metal chelators include EDTA, DTPA, and o-phenanthroline. Alkylators include compounds such as iodoacetamide. Porphyrins include porphine, its substituted forms, and metal complexes. Pyrenes include pyrene and other pyrene-based carboxylic acids that can be conjugated using protocols similar to those specified above.

The term phospholipid as used herein includes those compounds which upon hydrolysis yield phosphoric acid, an alcohol and one or more fatty acids. Representative examples of phospholipids include lecithin, cephalin and sphingomyelin.

As used in the present invention, groups that enhance the pharmacodynamic properties include groups that improve oligonucleotide uptake, enhance oligonucleotide resistance to degradation, and/or strengthen sequence-specific hybridization with RNA. Groups that enhance the pharmacokinetic properties, in the context of this invention, include groups that improve oligonucleotide uptake, distribution, metabolism or excretion.

For the purposes of this invention, the terms "reporter molecule" and "reporter enzyme" are inclusive of those molecules or enzymes that have physical or chemical properties that allow them to be identified in gels, fluids, whole cellular systems, broken cellular systems and the like utilizing physical properties such as spectroscopy, radioactivity, calorimetric assays, fluorescence, and specific binding. Particularly useful as reporter molecules are fluorophores, chromaphores and radiolabel-containing moieties. Fluorophores are molecules detectable by fluoresence spectroscopy. Examples of preferred fluorophores are fluorescein and rhodamine dyes and acridines. There are numerous commercial available fluorophores including "Texas Red" and other like fluoresceins and rhodamines available for Molecular Probes, Eugene, Oreg. Chromaphores are molecules capable of detection by visible or ultraviolet (UV-VIS) absorbance spectroscopy. Example of chromaphores are polynuclear aromatics such as anthracene, perylene, pyrene, rhodamine and chrysene. Radiolabel-containing moieties, as used herein, are molecules incorporating at least one radioactive atom, such as $^3H$ or $^{14}C$, enabling detection thereby. Reporter enzymes may be detected directly or via their enzymatic products by any of the methods mentioned above. Particularly useful as reporter enzymes are alkaline phosphatase and horseradish peroxidase.

Steroid molecules according to the invention include those chemical compounds that contain a perhydro-1,2-cyclopentanophenanthrene ring system. Particularly useful as steroid molecules are the bile acids including cholic acid, deoxycholic acid and dehydrocholic acid; steroids including cortisone, digoxigenin, testosterone and cholesterol and cationic steroids such as cortisone having a trimethylaminomethyl hydrazide group attached via a double bond at the 3-position of the cortisone ring (3-trimethylaminomethylhydrazido cortisone).

Proteins and peptides are utilized in their usual sense as polymers of amino acids. Normally peptides comprise such polymers that contain a smaller number of amino acids per unit molecule than do the proteins. Particularly useful as peptides and proteins are sequence-specific peptides and proteins including phosphodiesterases, peroxidases, phosphatases and nucleases. Such peptides and proteins include, but are not limited to, SV40 peptide, RNase A, RNase H and Staphylococcal nuclease.

Lipophilic molecules include naturally-occurring and synthetic aromatic and non-aromatic moieties such as fatty acids, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene. Particularly useful as lipophilic molecules are alicyclic hydrocarbons, saturated and unsaturated fatty acids, waxes, terpenes and polyalicyclic hydrocarbons including adamantane and buckminsterfullerenes.

Alkylators according to the invention are moieties that can effect attachment of electrophilic groups to targeted molecular structures. Representative alkylators are disclosed by Meyer, et al., *J. Am. Chem. Soc.* 1989, 111, 8517.

Intercalators are polycyclic aromatic moieties that can insert between adjacent base pairs without affecting normal Watson-Crick base pairing, and include hybrid intercalator/ligands such as the photonuclease/intercalator ligand 6-[[[9-[[6-(4-nitrobenzamido)hexyl]amino]acridin-4-yl]carbonyl]amino]hexanoylpentafluorophenyl ester. This compound has two noteworthy features: an acridine moiety that is an intercalator and a p-nitrobenzamido group that is a photonuclease. Other representative intercalators are disclosed by Manoharan, M., *Antisense Research and Applications*, Crooke and Lebleu, eds., CRC Press, Boca Raton, 1993.

Cell receptor binding molecules according to the invention are vitamins and carbohydrate moieties for which specific receptors exist within a cell. Representative cell receptor binding molecules are disclosed by application Ser. No. PCT/US92/09196, filed Oct. 23, 1992, the content of which are incorporated herein by reference.

Crosslinking agents are moieties that can effect intrastrand or interstrand covalent binding of RNA and/or DNA, and include photo-crosslinking agents. Examples of photo-crosslinking agents include aryl azides such as N-hydroxysuccinimidyl-4-azidobenzoate (HSAB) and N-succinimidyl-6(-4'-azido-2'-nitrophenylamino)hexanoate (SANPAH). Aryl azides conjugated to oligomers will effect crosslinking with nucleic acids and proteins upon irradiation. Other representative crosslinking agents are disclosed in International Patent Application Serial No. PCT/US93/02059, filed Mar. 5, 1993, which is incorporated herein by reference.

Useful crown amines are disclosed by Studer, et al., *Helv. Chim. Acta* 1986, 69, 2081 and Smith-Jones, et al., *Bioconjugate Chem.* 1991, 2, 415.

Vitamins according to the invention generally can be classified as water soluble or lipid soluble. Water solubl vitamins include thiamine, riboflavin, nicotinic acid or niacin, the vitamin $B_6$ pyridoxal group, pantothenic acid, biotin, folic acid, the $B_{12}$ cobalamin coenzymes, inositol, choline and ascorbic acid. Lipid soluble vitamins include the vitamin A family, vitamin D, the vitamin E tocopherol family and vitamin K (and phytols). The vitamin A family, including retinoic acid and retinol, are absorbed and transported to target tissues through their interaction with specific proteins such as cytosol retinol-binding protein type II (CRBP-II), Retinol-binding protein (RBP), and cellular retinol-binding protein (CRBP). These proteins, which have been found in various parts of the human body, have molecular weights of approximately 15 kD. They have specific interactions with compounds of the vitamin A family, especially, retinoic acid and retinol.

The vitamin A family of compounds can be attached to oligomers of the invention via acid or alcohol functionalities found in the various family members. For example, conjugation of an N-hydroxysuccinimide ester of an acid moiety of retinoic acid to an amine function of a pendant group of the oligomer results in linkage of the vitamin A compound to the oligomer, via an amide bond. In similar fashion, standard esterification chemistries may be used to attach the acid moiety of the retinoic acid group to a 4'-oxygen of a compound of the invention, or to a hydroxyl function of a pendent group thereof.

α-Tocopherol (vitamin E) and other tocopherols (beta through zeta) can be similarly conjugated to oligomers also to enhance uptake due to their lipophilic character. The liophilic vitamin, vitamin D, and its ergosterol precursors can be conjugated to oligomers through their hydroxyl groups by first activating the hydroxyl groups by forming, for example, hemisuccinate esters. Conjugation then is effected, as for instance, to an aminolinker pendant from the oligomer, or through other suitable functional groups described herein. Other vitamins that can be conjugated to oligomers through hydroxyl groups on the vitamins include thiamine, riboflavin, pyridoxine, pyridoxamine, pyridoxal, deoxypyridoxine. Lipid soluble vitamin K's and related quinone-containing compounds can be conjugated via carbonyl groups on the quinone ring. The phytol moiety of vitamin K may also serve to enhance binding of the oligomers to cells.

Pyridoxal phosphate is the coenzyme form of Vitamin $B_6$. Vitamin $B_6$ is also known as pyridoxine. Pyridoxal has specific $B_6$-binding proteins. The role of these proteins in pyridoxal transport has been studied by Zhang and McCormick, *Proc. Natl. Acad. Sci. USA*, 1991 88, 10407. Zhang and McCormick showed that a series of N-(4'-pyridoxyl)amines, in which several synthetic amines were conjugated at the 4'-position of pyridoxal, were able to enter cells by a process facilitated by the $B_6$ transporter. Zhang and McCormick also demonstrated the release of these synthetic amines within the cell. Other pyridoxal family members include pyridoxine, pyridoxamine, pyridoxal phosphate, and pyridoxic acid. Pyridoxic acid, niacin, pantothenic acid, biotin, folic acid and ascorbic acid can be conjugated to oligomers using N-hydroxysuccinimide esters as described above for retinoic acid.

The compounds of the invention are resistant to nuclease degradation and are capable of modulating the activity of DNA and RNA.

The term "nucleoside" as used in connection with this invention refers to a unit made up of a heterocyclic base and its sugar. The term "nucleotide" refers to a nucleoside having a phosphate group on its 3' or 5' sugar hydroxyl group.

As used herein, the term "oligonucleotide" is intended to include both naturally occurring and non-naturally occurring (i.e., "synthetic") oligomers of linked nucleosides. Although such linkages generally are between the 3' carbon of one nucleoside and the 5' carbon of a second nucleoside (i.e., 3'–5' linkages), other linkages (such as 2'–5' linkages) can be formed.

Naturally occurring oligonucleotides are those which occur in nature; for example ribose and deoxyribose phosphodiester oligonucleotides having adenine, guanine, cytosine, thymine and uracil nucleobases. As used herein, non-naturally occurring oligonucleotides are oligonucleotides that contain modified sugar, internucleoside linkage and/or nucleobase moieties. Such oligonucleotide analogs are typically structurally distinguishable from, yet functionally interchangeable with, naturally occurring or synthetic wild type oligonucleotides. Thus, non-naturally occurring oligonucleotides include all such structures which function effectively to mimic the structure and/or function of a desired RNA or DNA strand, for example, by hybridizing to a target.

Representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see especially pages 622 and 623, and in the *Concise Encyclopedia of Polymer Science and Engineering*, J. I. Kroschwitz Ed., John Wiley & Sons, 1990, pages 858–859, Cook, *Anti-Cancer Drug Design* 1991, 6, 585–607, each of which are hereby incorporated by reference in their entirety). The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Representative 2'-substituents according to the present invention include H, OH, F, and groups of formula

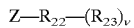

where:
Z is O, S, NH, or N—$R_{22}$—$(R_{23})_v$
$R_{22}$ is $C_1$–$C_{20}$ alkyl, $C_2$–$C_{20}$ alkenyl, or $C_2$–$C_{20}$ alkynyl;
$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;
v is from 0 to about 10.

Additional 2'-substituents have one of the formulas:

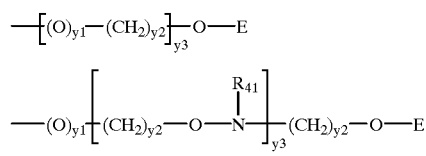

where:
y1 is 0 or 1;
y2 is 0 to 10;
y3 is 1 to 10;
E is $N(R_{41})(R_{42})$ or $N=C(R_{41})(R_{42})$; and
each $R_{41}$ and each $R_{42}$ is independently H, $C_1$–$C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O.

Preferred 2'-groups include H, OH, F, and O—, S—, or N-alkyl groups. One particularly preferred group includes 2'-methoxyethoxy [2'-O—$CH_2CH_2OCH_3$, also known as 2'-O-(2-methoxyethyl) or 2'-MOE] (Martin et al., *Helv. Chim. Acta*, 1995, 78, 486), i.e., an alkoxyalkoxy group. A further preferred modification includes 2'-dimethylaminooxyethoxy, i.e., a $O(CH_2)_2ON(CH_3)_2$ group, also known as 2'-DMAOE, as described in co-owned U.S. patent application Ser. No. 09/016,520, filed on Jan. 30, 1998, the contents of which are herein incorporated by reference. Other preferred modifications include 2'-methoxy (2'-O—$CH_3$) and 2'-aminopropoxy (2'—$OCH_2CH_2CH_2NH_2$).

Sugars having O-substitutions on the ribosyl ring are also amenable to the present invention. Representative substitutions for ring O include S, $CH_2$, CHF, and $CF_2$, see, e.g., Secrist, et al., *Abstract 21, Program & Abstracts, Tenth International Roundtable, Nucleosides, Nucleotides and their Biological Applications*, Park City, Utah, Sep. 16–20, 1992, hereby incorporated by reference in its entirety. Additionial modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327;

Svinarchuk et al., *Biochimie*, 1993, 75, 49), a phospholipid, e.g., dihexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety Crooke et al., *J. Pharmacol. Exp. Ther.*, 1996, 277, 923).

As used herein, the term "alkyl" includes but is not limited to straight chain, branch chain, and cyclic unsaturated hydrocarbon groups including but not limited to methyl, ethyl, and isopropyl groups. Alkyl groups of the present invention may be substituted. Representative alkyl substituents are disclosed in U.S. Pat. No. 5,212,295, at column 12, lines 41–50, hereby incorporated by reference in its entirety.

Alkenyl groups according to the invention are to straight chain, branch chain, and cyclic hydrocarbon groups containing at least one carbon-carbon double bond, and alkynyl groups are to straight chain, branch chain, and cyclic hydrocarbon groups containing at least one carbon-carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example morpholino groups. As used herein, the term "heterocycloalkenyl" denotes a ring system having one or more double bonds, and one or more heteroatoms. Preferred heterocycloalkenyl groups include, for example, pyrrolidino groups.

Oligonucleotides according to the present invention that are hybridizable to a target nucleic acid preferably comprise from about 5 to about 50 nucleosides. It is more preferred that such compounds comprise from about 8 to about 30 nucleosides, with 15 to 25 nucleosides being particularly preferred. As used herein, a target nucleic acid is any nucleic acid that can hybridize with a complementary nucleic acid-like compound. Further in the context of this invention, "hybridization" shall mean hydrogen bonding, which may be Watson-Crick, Hoogsteen or reversed Hoogsteen hydrogen bonding between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric compound to non-target sequences under conditions in which specific binding is desired, i.e. under physiological conditions in the case of in vivo assays or therapeutic treatment, or in the case of in vitro assays, under conditions in which the assays are performed.

Phosphorothioate linkages in the oligonucleotides of the invention are prepared using standard phosphoramidite chemistry on, for example, an automated DNA synthesizer (e.g., Applied Biosystems model 380B) and oxidation with 0.2 M solution of 3H-1,2-benzodithiole-3-one 1,1-dioxide in acetonitrile for the stepwise thiation of the phosphite linkages. Phosphorothioate linkages that have Sp configuration can be prepared generally according to the procedures described in U.S. Pat. Nos. 5,212,295, 5,587,361 and 5,599,797. In preferred embodiments, 2'-modified amidites are used to synthesize compounds of the invention according to standard phosphoramidite regimes. In especially preferred embodiments, the amidites have a 2'-methoxyethoxy ($-O-CH_2-CH_2-O-CH_3$, "MOE") substituent.

As will be recognized, this invention concerns oligonucleotides that exhibit increased stability relative to their naturally occurring counterparts. Extracellular and intracellular nucleases generally do not recognize (and, therefore, do not bind to) the compounds of the invention. The modified internucleoside linkages of this invention preferably replace naturally-occurring phosphodiester-5'-methylene linkages to confer nuclease resistance.

The oligonucleotides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

Some representative therapeutic indications and other uses for the compounds of the invention are as follows. One therapeutic indication of particular interest is psoriasis. Psoriasis is a common chronic and recurrent disease characterized by dry, well-circumscribed, silvery, scaling papules and plaques of various sizes. The disease varies in severity from a few lesions to widespread dermatosis with disabling arthritis or exfoliation. The ultimate cause of psoriasis is not known, but the thick scaling that occurs is probably due to increased epidermal cell proliferation (*The Merck Manual of Diagnosis and Therapy*, 15th Ed., pp. 2283–2285, berkow et al., eds., Rahway, N.J., 1987). Inhibitors of Protein Kinase C (PKC) have been shown to have both antiproliferative and anti-inflammatory effects in vitro. Some antipsoriasis drugs, such as cyclosporin A and anthralin, have been shown to inhibit PKC, and inhibition of PKC has been suggested as a therapeutic approach to the treatment of psoriasis (Hegemann, L. and G. Mahrle, *Pharmacology of the Skin*, H. Mukhtar ed., pp. 357–368, CRC Press, Boca Raton, Fla., 1992). Antisense compounds targeted to Protein Kinase C (PKC) protein are described in U.S. Pat. No. 5,620,963 to Cook et al. and U.S. Pat. No. 5,681,747 to Boggs et al.

Another type of therapeutic indication of interest is inflammatory disorders of the skin. These occur in a variety of forms including, for example, lichen planus, toxic epidermal necrolyis (TEN), ertythema multiforme and the like (*The Merck Manual of Diagnosis and Therapy*, 15th Ed., pp. 2286–2292, Berkow et al., eds., Rahway, N.J., 1987). Expression of ICAM-1 has been associated with a variety of inflammatory skin disorders such as allergic contact dermatitis, fixed drug eruption, lichen planus and psoriasis (Ho et al., *J. Am. Acad. Dermatol.*, 1990, 22, 64; Griffiths et al., *Am. J. Pathology*, 1989, 135, 1045; Lisby et al., *Br. J. Dermatol.*, 1989, 120, 479; Shiohara et al., *Arch. Dermatol.*, 1989, 125, 1371; Regezi et al., *Oral Surg. Oral Med. Oral Pathol.*, 1996, 81, 682). Moreover, intraperitoneal administration of a monoclonal antibody to ICAM-1 decreases ovalbumin-induced eosinophil infiltration into skin in mice (Hakugawa et al., *J. Dermatol.*, 1997, 24, 73). Antisense compounds targeted to ICAM-1 are described in U.S Pat. Nos. 5,514,788 and 5,591,623, and co-pending U.S. patent applications Ser. Nos. 09/009,490 and 09/062,416, Jan. 20, 1998 and Apr. 17, 1998, respectively, all to Bennett et al.

Other antisense targets for skin inflammatory disorders are VCAM-1 and PECAM-1. Intraperitoneal administration of a monoclonal antibody to VCAM-1 decreases ovalbumin-induced eosinophil infiltration into the skin of mice (Hakugawa et al., *J. Dermatol.*, 1997, 24, 73). Antisense compounds targeted to VCAM-1 are described in U.S. Pat. Nos. 5,514,788 and 5,591,623. PECAM-1 proteins are glycoproteins which are expressed on the surfaces of a variety of cell types (for reviews, see Newman, *J. Clin. Invest.*, 1997, 99, 3 and DeLisser et al., *Immunol. Today*, 1994, 15, 490). In addition to directly participating in cell-cell interactions, PECAM-1 apparently also regulates the activity and/or expression of other molecules involved in cellular interactions (Litwin et al., *J. Cell Biol.*, 1997, 139, 219) and is thus a key mediator of several cell:cell interactions. Antisense compounds targeted to PECAM-1 are described in co-pending U.S. patent application Ser. No. 09/044,506, filed Mar. 19, 1998, by Bennett et al.

Another type of therapeutic indication of interest for oligonucleotides encompasses a variety of cancers of the skin. Representative skin cancers include benign tumors (warts moles and the like) and malignant tumors such as, for example, basal cell carcinoma, squamous cell carcinoma, malignant melanoma, Paget's disease, Kaposi's sarcoma and the like (*The Merci Manual of Diagnosis and Therapy*, 15th Ed., pp. 2301–2310, Berkow et al., eds., Rahway, N.J., 1987). A number of molecular targets involved in tumorigenesis, maintenance of the hyperproliferative state and metastasis are targeted to prevent or inhibit skin cancers, or to prevent their spread to other tissues.

The ras oncogenes are guanine-binding proteins that have been implicated in cancer by, e.g., the fact that activated ras oncogenes have been found in about 30% of human tumors generally; this figure approached 100% in carcinomas of the exocrine pancreas (for a review, see Downward, *Trends in Biol. Sci.*, 1990, 15, 469). Antisense compounds targeted to H-ras and K-ras are described in U.S. Pat. No. 5,582,972 to Lima et al., U.S. Pat. No. 5,582,986 to Monia et al. and U.S. Pat. No. 5,661,134 to Cook et al., and in published PCT application WO 94/08003.

Protein Kinase C (PKC) proteins have also been implicated in tumorigenesis. Antisense compounds targeted to Protein Kinase C (PKC) proteins are described in U.S. Pat. No. 5,620,963 to Cook et al. and U.S. Pat. No. 5,681,747 to Boggs et al. Also of interest are AP-1 subunits and JNK proteins, particularly in regard to their roles in tumorigenesis and metastasis. The process of metastasis involves a sequence of events wherein (1) a cancer cell detaches from its extracellular matrices, (2) the detached cancer cell migrates to another portion of an animal's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, *Sci. Amer.*, 1996, 275, 72). However, many human tumors have elevated levels of activity of one or more matrix metalloproteinases (MMPs) (Stetler-Stevens on et al., *Annu. Rev. Cell Biol.*, 1993, 9, 541; Bernhard et al., *Proc. Natl. Acad. Sci. (U.S.A.)*, 1994, 91, 4293. The MMPs are a family of enzymes which have the ability to degrade components of the extracellular matrix (Birkedal-Hansen, *Current Op. Biol.*, 1995, 7, 728). In particular, one member of this family, matrix metalloproteinase-9 (MMP-9), is often found to be expressed only in tumors and other diseased tissues (Himelstein et al., *Invasion & Metastasis*, 1994, 14, 246).

Several studies have shown that regulation of the MMP-9 gene may be controlled by the AP-1 transcription factor (Kerr et al., *Science*, 1988, 242, 1242; Kerr et al., *Cell*, 1990, 61, 267; Gum et al., *J. Biol. Chem.*, 1996, 271, 10672; Hua et al., *Cancer Res.*, 1996, 56, 5279). Inhibition of AP-1 function has been shown to attenuate MMP-9 expression (U.S. patent application Ser. No. 08/837,201). AP-1 is a heterodimeric protein having two subunits, the gene products of fos and jun. Antisense compounds targeted to c-fos and c-jun are described in co-pending U.S. patent application Ser. No. 08/837,201, filed Mar. 14, 1997, by Dean et al.

Furthermore, AP-1 is itself activated in certain circumstances by phosphorylation of the Jun subunit at an amino-terminal position by Jun N-terminal kinases (JNKs). Thus, inhibition of one or more JNKs is expected to result in decreased AP-1 activity and, consequentially, reduced MMP expression. Antisense compounds targeted to JNKs are described in co-pending U.S. patent application Ser. No. 08/910,629, filed Aug. 13, 1997, by Dean et al.

Infectious diseases of the skin are caused by viral, bacterial or fungal agents. In the case of Lyme disease, the tick borne causative agent thereof, the spirochete Borrelia burgdorferi, up-regulates the expression of ICAM-1, VCAM-1 and ELAM-1 on endothelial cells in vitro (Boggemeyer et al., *Cell Adhes. Comm.*, 1994, 2, 145). Furthermore, it has been proposed that the mediation of the disease by the anti-inflammatory agent prednisolone is due in part to mediation of this up-regulation of adhesion molecules (Hurtenbach et al., *Int. J. Immunopharmac.*, 1996, 18, 281). Thus, potential targets for therapeutic mediation (or prevention) of Lyme disease include ICAM-1, VCAM-1 and ELAM-1 supra).

Other infectious disease of the skin which are tractable to treatment using the compositions and methods of the invention include disorders resulting from infection by bacterial, viral or fungal agents (*The Merck Manual of Diagnosis and Therapy*, 15th Ed., pp. 2263–2277, Berkow et al., ed., Rahway, N.J., 1987).

With regards to infections of the skin caused by fungal Regents, U.S. Pat. No. 5,691,461 provides antisense compounds for inhibiting the growth of *Candida albicans*.

With regards to infections of the skin caused by viral asents, U.S. Pat. Nos. 5,166,195, 5,523,389 and 5,591,600 provide oligonucleotide inhibitors of Human Immunodeficiency Virus (HIV). U.S. Pat. No. 5,004,810 provides oligomers capable of hybridizing to herpes simplex virus Vmw65 mRNA and inhibiting its replication. U.S. Pat. Nos. 5,194,428 and 5,580,767 provide antisense compounds having antiviral activity against influenzavirus. U.S. Pat. No. 4,806,463 provides antisense compounds and methods using them to inhibit HTLV-III replication. U.S. Pat. Nos. 4,689,320, 5,442,049, 5,591,720 and 5,607,923 are directed to antisense compounds as antiviral agents specific to cytomegalovirus (CMV). U.S. Pat. No. 5,242,906 provides antisense compounds useful in the treatment of latent Epstein-Barr virus (EBV) infections. U.S. Pat. Nos. 5,248,670, 5,514,577 and 5,658,891 provide antisense compounds useful in the treatment of herpesvirus infections. U.S. Pat. Nos. 5,457,189 and 5,681,944 provide antisense compounds useful in the treatment of papillomavirus infections. The antisense compounds disclosed in these patents, which are herein incorporated by reference, may be used with the compositions of the invention to effect prophylactic, palliative or therapeutic relief from diseases caused or exacerbated by the indicated pathogenic agents.

Antisense oligonucleotides employed in the compositions of the present invention may also be used to determine the nature, function and potential relationship of various genetic components of the body to disease or body states in animals. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development since the "knock-out" mutation would produce a lethal phenotype. Moreover, the loss-of-function phenotype cannot be transiently introduced during a particular part of the animal's life cycle or disease state; the "knock-out" mutation is always present. "Antisense knockouts," that is, the selective modulation of expression of a gene by antisense oligonucleotides, rather than by direct genetic manipulation, overcomes these limitations (see, for example, Albert et al., *Trends in Pharmacological Sciences*, 1994, 15, 250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. Antisense oligonucleotides have been systemically administered to rats in order to study the role of the N-methyl-D-aspartate receptor in neuronal death, to mice in order to investigate the biological role of protein kinase C-a, and to rats in order to examine the role of the neuropeptide Y1 receptor in anxiety (Wahlestedt et al., *Nature*, 1993, 363:260; Dean et al., *Proc. Natl. Acad. Sci. U.S.A.*, 1994, 91:11762; and Wahlestedt et al., *Science*, 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.*, 1994, 15:250). By providing compositions and methods for the simple non-parenteral delivery of oligonucleotides and other nucleic acids, the present invention overcomes these and other shortcomings.

The administration of therapeutic or pharmaceutical compositions comprising the oligonucleotides of the invention is believed to be within the skill of those in the art. In general, a patient in need of therapy or prophylaxis is administered a composition comprising a compound of the invention, commonly in a pharmaceutically acceptable carrier, in doses ranging from 0.01 ug to 100 g per kg of body weight depending on the age of the patient and the severity of the disorder or disease state being treated. Dosing is dependent on severity and responsiveness of the disease state to be treated, with the course of treatment lasting from several days to several months, or until a cure is effected or a diminution or prevention of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual antisense compounds, and can generally be estimated based on $EC_{50}$s found to be effective in in itro and in vivo animal models.

In the context of the invention, the term "treatment regimen" is meant to encompass therapeutic, palliative and prophylactic modalities of administration of one or more compositions of the invention. A particular treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the composition may either be increased in the event the patient does not respond significantly to current dosage levels, or the dose may be decreased if an alleviation of the symptoms of the disorder or disease state is observed, or if the disorder or disease state has been ablated.

An optimal dosing schedule is used to deliver a therapeutically effective amount of the oligonucleotide of the invention. The term "therapeutically effective amount," for the purposes of the invention, refers to the amount of oligonucleotide-containing pharmaceutical composition which is effective to achieve an intended purpose without undesirable side effects (such as toxicity, irritation or allergic response). Although individual needs may vary, determination of optimal ranges for effective amounts of pharmaceutical compositions is within the skill of the art. Human doses can be extrapolated from animal studies (Katocs et al. Chapter 27 In: *Remington's Pharmaceutical Sciences*, 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al. Chapter 3 In: *Goodman & Gilman's The Pharmacological Basis of Therapeutics*, 9th Ed., Hardman et al., eds., McGraw-Hill, New York, N.Y., 1996).

Following successful treatment, it may be desirable to have the patient undergo maintenance therapy to prevent the recurrence of the disease state, wherein the bioactive agent is administered in maintenance doses, ranging from 0.01 ug to 100 g per kg of body weight, once or more daily, to once every 20 years. For example, in the case of in individual known or suspected of being prone to an autoimmune or inflammatory condition, prophylactic effects may be achieved by administration of preventative doses, ranging from 0.01 ug to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

Prophylactic modalities for high risk individuals are also encompassed by the invention. As used herein, the term "high risk individual" is meant to refer to an individual for whom it has been determined, via, e.g., individual or family history or genetic testing, that there is a significantly higher than normal probability of being susceptible to the onset or recurrence of a disease or disorder. For example, a subject animal could have a personal and/or family medical history that includes frequent occurrences of a particular disease or disorder. As another example, a subject animal could have had such a susceptibility determined by genetic screening according to techniques known in the art (see, e.g., U.S. Congress, Office of Technology Assessment, Chapter 5 In: *Genetic Monitoring and Screening in the Workplace*, OTA-BA-455, U.S. Government Printing Office, Washington, D.C., 1990, pages 75–99). As part of a treatment regimen for a high risk individual, the individual can be prophylactically treated to prevent the onset or recurrence of the disease or disorder. The term "prophylactically effective amount" is meant to refer to an amount of a pharmaceutical composition which produces an effect observed as the prevention of the onset or recurrence of a disease or disorder. Prophylactically effective amounts of a pharmaceutical composition are typically determined by the effect they have compare to the effect observed when a second pharmaceutical composition lacking the active agent is administered to a similarly situated individual.

For therapeutic use the oligonucleotide analog is administered to an animal suffering from a disease modulated by some protein. It is preferred to administer to patients suspected of suffering from such a disease an amount of oligonucleotide analog that is effective to reduce the symptomology of that disease. One skilled in the art can determine optimum dosages and treatment schedules for such treatment regimens.

It is preferred that the RNA or DNA portion which is to be modulated be preselected to comprise that portion of DNA or RNA which codes for the protein whose formation or activity is to be modulated. The targeting portion of the composition to be employed is, thus, selected to be complementary to the preselected portion of DNA or RNA, that is to be an antisense oligonucleotide for that portion.

In accordance with one preferred embodiment of this invention, the compounds of the invention hybridize to HIV mRNA encoding the tat protein, or to the TAR region of HIV mRNA. En another preferred embodiment, the compounds mimic the secondary structure of the TAR region of HIV mRNA, and by doing so bind the tat protein. Other preferred compounds complementary sequences for herpes, papilloma and other viruses.

It is generally preferred to administer the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

This invention is also directed to methods for the selective binding of RNA for research and diagnostic purposes. Such selective, strong binding is accomplished by interacting such RNA or DNA with compositions of the invention which are resistant to degradative nucleases and which hybridize more strongly and with greater fidelity than known oligonucleotides or oligonucleotide analogs.

Additional objects, advantages, and novel features of this invention will become apparent to those skilled in the art upon examination of the following examples thereof, which are intended to be illustrative and not intended to be limiting.

EXAMPLE 1

Preparation of Oligonucleotides

Oligonucleotide Synthesis

Oligonucleotides were synthesized on a Perseptive Biosystems Expedite 8901 Nucleic Acid Synthesis System. The following summarizes the 1-$\mu$mol scale synthesis protocol. Two synthesizers were used. One was set up to run the diester (P=O) protocol and the other to run the thioate (P=S) protocol. Trityl groups were removed with trichloroacetic acid (975 $\mu$L over one minute) followed by an acetonitrile wash.

Phosphodiester (P=O) Protocol

All standard 2'-deoxy amidites (0.1M) were coupled twice per cycle (total coupling time was approximately 4 minutes). All novel (2'-modified) amidites were dissolved in dry acetonitrile (100 mg of amidite/1 mL acetonitrile) to give approximately 0.08–0.1 M solutions. Total coupling time was approximately 6 minutes (105 $\mu$L of amidite delivered). 1-H-tetrazole in acetonitrile was used as the activating agent. Excess amidite was washed away with acetonitrile. (1S)-(+)-(10-camphorsulfonyl) oxaziridine (CSO, 1.0 g CSO/8.72 ml dry acetonitrile) was used to oxidize (4 minute wait step) delivering approximately 375 $\mu$L of oxidizer.

Thioate (P=S) Protocol

The same amounts of amidites and reagents were delivered to the columns using the thioate protocol, except that the amount of oxidizer, 3H-1,2-benzodithiole-3-one-1,1-dioxide (Beaucage reagent, 3.4 g Beaucage reagent/200 mL acetonitrile), was 225 $\mu$L (one minute wait step). In both protocols, unreacted functionalities were capped with a 50:50 mixture of tetrahyrdofuran/acetic anhydride and tetrahydrofuran/pyridine/1-methyl imidazole. Trityl yields were followed by the trityl monitor during the duration of the synthesis. The final DMT group was left intact.

10 $\mu$mole Protocols

Approximately 300 mg CPG was used for each 10 $\mu$mole synthesis. For the diester (P=O) couplings, the following protocol was used: Trityl group removal was done using 7.5 mLs of trichloracetic acid. Coupling of both standard and novel amidites (0.8–0.1M) was achieved using a 23 minute coupling cycle with approximately 750 $\mu$L of amidite delivered. Approximately 2.7 mL of oxidizer (CSO) was delivered over 3 minutes. The capping was done over 80 seconds with 1.8 mLs of a 50:50 mixture of tetrahyrdofuran/acetic anhydride and tetrahydrofuran/pyridine/1-methyl imidazole.

The thioate (P=S) couplings removed the trityl groups with 7.5 mLs of trichloroacetic acid. Couplings of standard 0.1M amidites were accomplished using 750 μL of solution over 6.6 minutes. The novel amidite couplings were done using 750 μL of 0.08–0.1M solutions, delivered over 23 minutes. Approximately 2.7 mL of oxidizer was delivered over 3 minutes. The capping was done over 80 seconds with 1.8 mLs of a 50:50 mixture of tetrahyrdofuran/acetic anhydride and tetrahydrofuran/pyridine/1-methyl imidazole.

At 55° C., the 1 μmole syntheses were deprotected and cleaved from the CPG in 1–2 mL 28.0–30% ammonium hydroxide ($NH_4OH$) for approximately 16 hours. The 10 μmole synthesis CPG's was split into 2 vials for cleavage as described above. 5 mg $NH_4OH$ was added to each vial.

Oligonucleotide Purification

After the deprotection step, the samples were filtered from CPG using Gelman 0.45 um nylon acrodisc syringe filters. Excess $NH_4OH$ was evaporated away in a Savant AS160 automatic speed vac. The crude yield was measure on a Hewlett Packard 8452A Diode Array Spectrophotometer at 260 nm. Crude samples were then analyzed by mass spectrometry (MS) on a Hewlett Packard electrospray mass spectrometer. Trityl-on oligos were purified by reverse phase preparative high performance liquid chromatography (HPLC). HPLC conditions were as follows: Waters 600E with 991 detector; Waters Delta Pak C4 column (7.8×300 mm); Solvent A: 50 mM triethylammonium acetate (TEA-Ac), pH 7.0; B: 100% acetonitrile; 2.5 mL/min flow rate; the gradient for 22592 and 25303: 5% B for first five minutes with linear increase in B to 80% during the next 55 minutes. The gradient for 18268: 5% B for first five minutes with linear increase in B to 60% during the next 55 minutes. Fractions containing the desired product were collected and the solvent was dried off in the speed vac. Oligos were detritylated in 80% acetic acid for approximately 60 minutes and lyophilized again. Free trityl and excess salt were removed by passing detritylated oligos through Sephadex G-25 (size exclusion chromatography) and collecting appropriate samples through a Pharmacia fraction collector. The solvent was again evaporated away in a speed vac. Purified oligos were then analyzed for purity by CGE, HPLC (flow rate: 1.5 mL/min; Waters Delta Pak C4 column, 3.9×300 mm), and MS. The final yield was determined by spectrophotometer at 260 nm.

$^{31}$P NMR Analysis $^{31}$P NMR analysis indicated the right number of P=O and P=S linkages. The P=S chemical shifts are dispersed over 2–3 ppm due to the diasteromeric nature of the P=S linkages.

The structures of the oligonucleotides, and their physical characteristics, are shown in Tables I and II, below:

TABLE I

Oligonucleotides containing Staggered PS/PO linkages

| Oligo # | ISIS # | Sequence (5'- 3') | Backbone | Chemistry | Target |
|---|---|---|---|---|---|
| 1 | 18268 [SEQ ID NO:1] staggered oligomer | 5'-TSCmOTSGOASGOTSAOGSCmO ASGOASGOGSAOGSCmOTSC-3' | P=S/P=O | 2'-O-MOE | Human ICAM-I |
| 2 | 22592 [SEQ ID NO:2] staggered gapmer | 5'-AsToGsCmoAsTo TsGsCsmCsmCsmCsmCmO CmsAoAsGoGsA-3' | P=S/P=O | 2'-O-MOE & 2'-H | mouse C-raf |
| 3 | 25303 [SEQ ID NO:3] staggered hemimer | 5'GsCmsCmsCmsAsAsGsCmsTsGsGsCmO ASTOCmSCmOGSTOCmSA-3' | P=S/p=O | 2'-O-MOE & 2'-H | Human ICAM-I |

[1]All nucleotides in bold are 2'-O-MOE (2'-O-$CH_2$-$CH_2$-O-$CH_3$)

TABLE II

Physical characteristics of Oligonucleotides Containing Staggered PS/PO linkages

| ISIS# | Sequence(5'-3')[1] | Expected Mass (g) | Observed Mass (g) | HPLC Retn. Time (min.)[2] | #ODs Purified (@ 260 nm) |
|---|---|---|---|---|---|
| 18268[SEQ ID NO:1] | 5'-TSCmOTSGOASGOTSAO GSCmOASGOASGOGSAOGSCmOTSCm-3' | 7863 | 7865 | 21.00 | 1000 |
| 22592[SEQ ID NO:2] | 5'-AsToGsCmoAsTo TsCsmTsGsCsmCsmCsmCmOCmsAoAsGoGsA-3' | 7138 | 7123 | 22.00 | 136 |
| 25303[SEQ ID NO:3] | 5'-GsCmsCmsCmsAsAsGsCmsTsGsGsCmO ASTOCmSCmOGSTOCmSA-3' | 7008 | 7006 | 22.00 | 1250 |

[1]All nucleosides in bold are 2'-O-MOE
[2]Conditions: Waters 600E with detector 991; Waters C4 column (3.9×300mm); Solvent A: 50 mM TEA-Ac, pH 7.0; B:100% acetonitrile; 1.5 mL/min. flow rate; Gradient: 5% B for first five minutes with linear increase in B to 60% during the next 55 minutes.

EXAMPLE 2

Tm Analysis

Tm analysis of modified oligomers of the ICAM-1 series is shown in Table III below:

TABLE III

Tm Values of Human ICAM-1 Antisense Oligonucleotide ISIS 3067 and Analogs Against RNA Target
5'-TCT GAG TAG CAG AGG AGC TC-3'[SEQ ID NO:4 ]

| Oligonucleotide | Modifications | Tm |
|---|---|---|
| ISIS 3067 [SEQ ID NO:5] | P=S,2'-deoxy DNA | 50.1 |
| ISIS 11910 [SEQ ID NO:4] | P=O,2'-deoxy DNA | 58.4 |
| ISIS 11159 [SEQ ID NO:6] | P=S,2'-MOE | 79.2 |
| ISIS 11158 [SEQ ID NO:7] | P=O,2'-MOE | 86.6 |
| ISIS 18268 [SEQ ID NO:8] | P=O/P=S,STAGGERED 2'-MOE | 84.0 |

It is significant ot note from the above data that all 2'-MOE oligomers have higher binding affinity than 2'-H oligomers. In addition, in the series, ISIS 11159, 11158 and 18269 (the staggered oligomer) have binding affinity between the P=O and P=S oligomers, but the Tm loss is not significant (2.6°).

EXAMPLE 3

ICAM-1 Expression
Oligonucleotide Treatment of HUVECs

Cells were washed three times with Opti-MEM (Life Technologies, Inc.) prewarmed to 37° C. Oligonucleotides were premixed with 10 µg/ml Lipofectin (Life Technologies, Inc.) in Opti-MEM, serially diluted to the desired concentrations, and applied to washed cells. Basal and untreated (no oligonucleotide) control cells were also treated with Lipofectin. Cells were incubated for 4 h at 37° C., at which time the medium was removed and replaced with standard growth medium with or without 5 mg/ml TNF-α (R & D Systems). Incubation at 37° C. was continued until the indicated times.

Quantitation of ICAM-1 Protein Expression by Fluorescence-activated Cell Sorter

Cells were removed from plate surfaces by brief trypsinization with 0.25% trypsin in PBS. Trypsin activity was quenched with a solution of 2% bovine serum albumin and 0.2% sodium azide in PBS (+Mg/Ca). Cells were pelleted by centrifugation (1000 rpm, Beckman GPR centrifuge), resuspended in PBS, and stained with 3 µl/$10^5$ cells of the ICAM-1 specific antibody, CD54-PE (Pharmingin). Antibodies were in cubated with the cells for 30 min at 4° C. in the dark, under gently agitation. Cells were washed by centrifugation procedures and then resuspended in 0.3 ml of FacsFlow buffer (Bector Dickinson) with 0.5% formaldehyde (Polysciences). Expression of cell surface ICAM-1 was then determined by flow cytometry using a Becton Dickinson FACScan. Percentage of the control ICAM-1 expression was calculated as follows: [(oligonucleotide-treated ICAM-1 value)–(basal ICAM-1 value)/(non-treated ICAM-1 value)–(basal ICAM-1 value)]. (Baker, Brenda, et. al. 2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells, *The Journal of Biological Chemistry*, 272, 11994–12000, 1997.)

The oligonucleotides used in the study described above are shown in Table IV, below. Results are shown in Figure I.

TABLE IV

Controlling P=S Linkages: ICAM-1 Activity with Alternating P=S/P=O Linkages in a Uniform 2'-modified Oligomer

| Isis # | Oligonucleotides Tested | |
|---|---|---|
| 16952 | TCTGAGTAGCAGAGGAGCTC | MOE, P=O [SEQ ID NO:9] |
| 16953 | GATCGCGTCGGACTATGAAG | Scrambled Control [SEQ ID NO:10] |
| 15537 | TCTGAGTAGCAGAGGAGCTC | MOE, P=S [SEQ ID NO:11] |
| 16954 | GATCGCGTCGGACTATGAAG | Scrambled Control [SEQ ID NO:12] |
| 18268 | TCTGAGTAGCAGAGGAGCTC* | MOE, P=S/P=O [SEQ ID NO:13] |

C=5-methyl -C in all sequences (except C*)
<sup>a</sup>same base composition

The scrambled oligomers 16953 and 16954, which have the same base composition as the parent sequence, serve as controls.

It can be seen that the ICAM-1 expression data (Figure I) reveal that the staggered oligomer 18268 is more efficacious than both P=O oligomer (16952) and P=S oligomer (15537) in HUVEC cells. The oligomers are presumably working by a direct binding RNase H independent mechanism.

It is intended that each of the patents, applications, printed publications, and other published documents mentioned or referred to in this specification be herein incorporated by reference in their entirety.

Those skilled in the art will appreciate that numerous changes, and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound comprising a plurality of covalently-bound 2'-modified nucleosides having the formula:

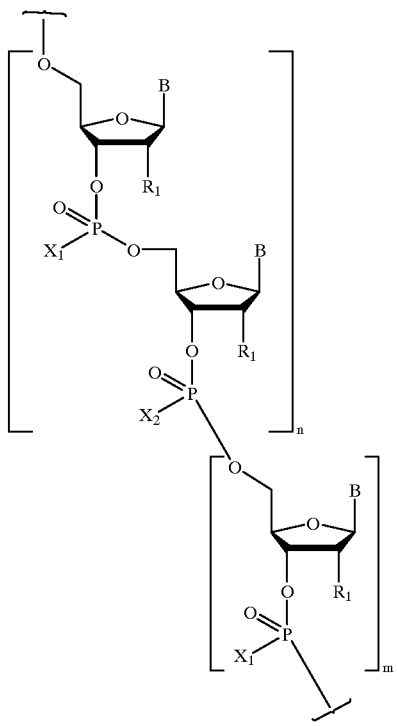

wherein:
each B is a nucleobase;
one of $X_1$ or $X_2$ is O, and the other of $X_1$ or $X_2$ is S;
each $R_1$ is F, or a group of formula $Z-R_{22}-(R_{23})_v$;
$Z$ is O, S, NH, or $N-R_{22}-(R_{23})_v$;
$R_{22}$ is $C_1-C_{20}$ alkyl, $C_2-C_{20}$ alkenyl, or $C_2-C_{20}$ alkynyl;
$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;
v is from 0 to about 10;
or $R_1$ has one of the formulas:

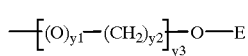

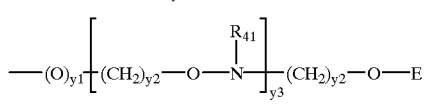

wherein:
y1 is 0 or 1;
y2 is 0 to 10, provided that y1 and y2 are not simultaneously 0;
y3 is 1 to 10;
E is $N(R_{41})(R_{42})$ or $N=C(R_{41})(R_{42})$;

each $R_{41}$ and each $R_{42}$ is independently H, $C_1-C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heterotom selected from N and O;
n is from 2 to 50; and
m is 0 or 1.

2. The compound of claim 1 wherein $R_1$ is $-O-CH_2-CH_2-O-CH_3$.

3. The compound of claim 1 wherein n is about 5 to about 50.

4. The compound of claim 1 wherein n is about 8 to about 30.

5. The compound of claim 1 wherein n is about 4 to about 15.

6. The compound of claim 1 wherein n is 2 to about 10.

7. An oligonucleotide having the Formula:

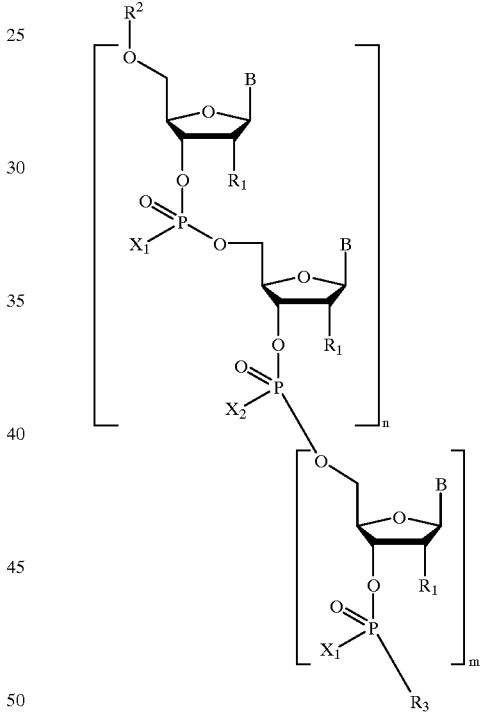

wherein:
each B is a nucleobase;
$X_1$ is S;
$X_2$ is O;
each $R_1$ is H, OH, F, or a group of formula $Z-R_{22}-(R_{23})_v$;
$Z$ is O, S, NH, or $N-R_{22}-(R_{23})_v$;
$R_{22}$ is $C_1-C_{20}$ alkyl, $C_2-C_{20}$ alkenyl, or $C_2-C_{20}$ alkynyl;
$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

v is from 0 to about 10;

or $R_1$ has one of the formulas:

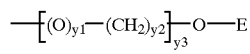

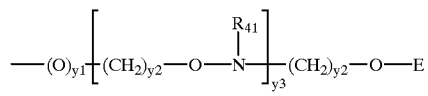

wherein:

y1 is 0 or 1;

y2 is 0 to 10, provided that y1 and y2 are not simultaneously 0;

y3 is 1 to 10;

E is $N(R_{41})(R_{42})$ or $N=C(R_{41})(R_{42})$;

each $R_{41}$ and each $R_{42}$ is independently H, $C_1$-$C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heterotom selected from N and O;

n is from 2 to 50;

m is 0 or 1;

$R_2$ is H, a hydroxyl protecting group, or an oligonucleotide; and $R_3$ is OH, an oligonucleotide, or a linker connected to a solid support.

8. The compound of claim 7 wherein $R_1$ is —O—$CH_2$—$CH_2$—O—$CH_3$.

9. The compound of claim 8 wherein $R_2$ is H, and $R_3$ is OH.

10. The compound of claim 8 wherein $R_2$ is a phosphodiester-linked oligonucleotide or a phosphorothioate linked oligonucleotide.

11. The compound of claim 8 wherein $R_3$ is a phosphodiester-linked oligonucleotide or a phosphorothioate linked oligonucleotide.

12. The compound of claim 8 wherein $R_2$ and $R_3$ are each a phosphodiester-linked oligonucleotide or a phosphorothioate linked oligonucleotide.

13. A compound having the Formula:

(5') $W^1$—$W^2$—$W^3$ (3')

wherein:

$W^1$ has the Formula:

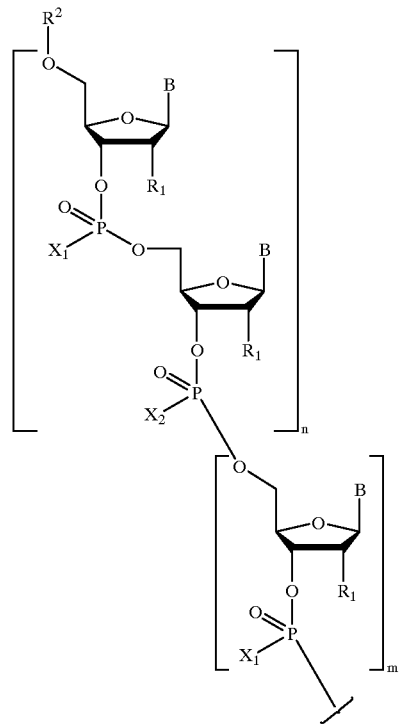

wherein:

each B is a nucleobase;

one of $X_1$ or $X_2$ is O, and the other of $X_1$ or $X_2$ is S;

each $R_1$ is H, OH, F, or a group of formula $Z$—$R_{22}$—$(R_{23})_v$;

Z is O, S, NH, or N—$R_{22}$—$(R_{23})_v$;

$R_{22}$ is $C_1$-$C_{20}$ alkyl, $C_2$-$C_{20}$ alkenyl, or $C_2$-$C_{20}$ alkynyl;

$R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, or polyether;

v is from 0 to about 10;

or $R_1$ has one of the formulas:

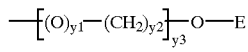

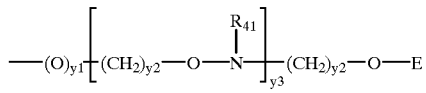

wherein:
y1 is 0 or 1;
y2 is 0 to 10, provided the y1 and y2 are not simultaneous 0;
y3 is 1 to 10;
E is $N(R_{41})(R_{42})$ or $N=C(R_{41})(R_{42})$;
each $R_{41}$ and each $R_{42}$ is independently H, $C_1$-$C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heterotom selected from N and O;
n is from 2 to 50;
m is 0 or 1;
$R_1$ is H, a hydroxyl protecting group, or an oligonucleotide;
$W^3$ has the Formula:

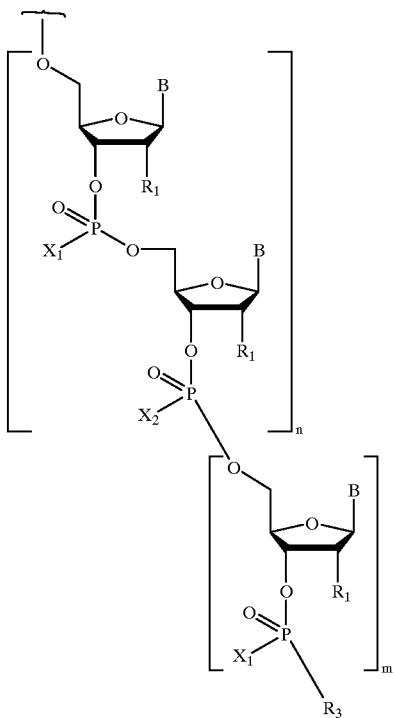

wherein $R_3$ is OH, an oligonucleotide, or a linker connected to a solid support; and $W^2$ is a plurality of covalently bound nucleosides linked by phosphodiester or phosphorothioate linkages.

14. The compound of claim 13 wherein $R_1$ is —O—$CH_2$—$CH_2$—O—$CH_3$.

15. The compound of claim 14 wherein $R_2$ is H, and $R_3$ is OH.

16. The compound of claim 14 wherein n is about 5 to about 50.

17. The compound of claim 14 wherein n is about 8 to about 30.

18. The compound of claim 14 wherein n is about 4 to about 15.

19. The compound of claim 14 wherein n is 2 to about 10.

20. The compound of claim 14 wherein $W^2$ is a plurality of covalently bound nucleosides linked by phosphodiester linkages.

21. The compound of claim 14 wherein $W^2$ is a plurality of covalently bound nucleosides linked by phosphorothioate linkages.

22. A composition comprising a compound of claim 1 and an acceptable carrier.

23. A composition comprising a compound of claim 7 and an acceptable carrier.

24. A composition comprising a compound of claim 12 and an acceptable carrier.

25. A method of assaying a nucleic acid, comprising contacting a solution suspected to contain said nucleic acid with a compound of claim 1.

26. A method of assaying a nucleic acid, comprising contacting a solution suspected to contain said nucleic acid with a compound of claim 7.

27. A method of assaying a nucleic acid, comprising contacting a solution suspected to contain said nucleic acid with compound of claim 13.

* * * * *